United States Patent [19]  [11]  4,113,664
Conrad et al.  [45]  Sep. 12, 1978

[54] 2,4-DIOXA-SPIRO(5,5)UNDEC-8-ENE PERFUME COMPOSITIONS

[75] Inventors: Jens Conrad, Hilden; Klaus Bruns, Krefeld-Traar, both of Fed. Rep. of Germany

[73] Assignee: Henkel Kommanditgesellschaft auf Aktien, Dusseldorf-Holthausen, Fed. Rep. of Germany

[21] Appl. No.: 765,531

[22] Filed: Feb. 4, 1977

[30] Foreign Application Priority Data

Feb. 6, 1976 [DE]  Fed. Rep. of Germany ....... 2604553

[51] Int. Cl.² .............................................. C11B 9/00
[52] U.S. Cl. ................................. 252/522; 260/340.7
[58] Field of Search ...................... 252/522; 260/340.7

[56] References Cited
U.S. PATENT DOCUMENTS 3,127,417  3/1964  Porret et al. ...................... 260/340.7

OTHER PUBLICATIONS

William G. Daubeu et al., Tetrahedron Letters, No. 8, pp. 515–517, 1975, also Chem. Ab. 83:10447d.
Christian S. Rondestvedt, Jr., J. Org. Chem., vol. 26, pp. 2247–2253, 1961.

Primary Examiner—Veronica O'Keefe
Attorney, Agent, or Firm—Hammond & Littell

[57] ABSTRACT

A perfumery composition consisting essentially of from 1% to 50% by weight of a 2,4-dioxa-spiro(5,5)undec-8-en of the formula

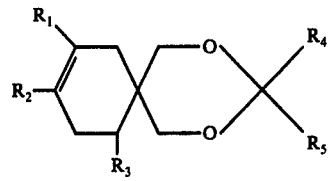

wherein $R_1$, $R_2$ and $R_3$ are members selected from the group consisting of hydrogen and methyl, $R_4$ is a member selected from the group consisting of hydrogen, alkyl having 1 to 4 carbon atoms, methoxy, ethoxy, vinyl and 1-propenyl, $R_5$ is a member selected from the group consisting of hydrogen and alkyl having 1 to 4 carbon atoms, and $R_4$ and $R_5$ taken together are —(CH$_2$)$_n$—where $n$ is an integer from 4 to 6, and the remainder, customery constituents of perfumery compositions. Some of the compounds are novel.

28 Claims, No Drawings

2,4-DIOXA-SPIRO(5,5)UNDEC-8-ENE PERFUME COMPOSITIONS

The present invention relates to perfumery compositions containing 2,4-dioxa-spiro(5,5)undec-8-ens and to some novel compounds.

OBJECTS OF THE INVENTION

An object of the present invention is the development of perfumery compositions with fragrances ranging from fruity, herbal, flowery to leather-like.

Another object of the present invention is the development of a perfumery composition consisting essentially of from 1 to 50% by weight of a 2,4-dioxa-spiro(5,5)undec-8-en of the formula

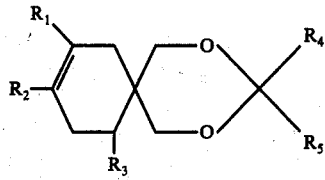

wherein $R_1$, $R_2$ and $R_3$ are members selected from the group consisting of hydrogen and methyl, $R_4$ is a member selected from the group consisting of hydrogen, alkyl having 1 to 4 carbon atoms, methoxy, ethoxy, vinyl and 1-propenyl, $R_5$ is a member selected from the group consisting of hydrogen and alkyl having 1 to 4 carbon atoms, methoxy, ethoxy, vinyl and 1-propenyl, $R_5$ is a member selected from the group consisting of hydrogen and alkyl having 1 to 4 carbon atoms, and $R_4$ and $R_5$ taken together are $-(CH_2)_n-$ where $n$ is an integer from 4 to 6, and the remainder customary constituents of perfumery compositions.

A further object of the present invention is the development of 2,4-dioxa-spiro(5,5)undec-8-ens selected from the group consisting of 3-methyl-2,4-dioxa-spiro(5,5)undec-8-en, 3-ethyl-2,4-dioxa-spiro(5,5)undec-8-en, 3-propyl-2,4-dioxa-spiro(5,5)undec-8-en, 3,3-dimethyl-2,4-dioxa-spiro(5,5) undec-8-en, 3-ethyl-3-methyl-2,4-dioxa-spiro(5,5)undec-8-en, a compound having the formula

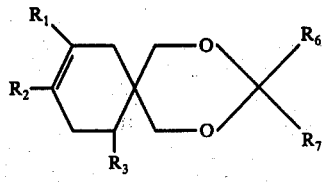

wherein $R_1$, $R_2$ and $R_3$ are members selected from the group consisting of hydrogen and methyl, $R_6$ is a member selected from the group consisting of methoxy and ethoxy, $R_7$ is a member selected from the group consisting of hydrogen and alkyl having 1 to 4 carbon atoms, and $R_6$ and $R_7$ taken together are $-(CH_2)_n-$ where $n$ an integer from 4 to 6, and a compound having the formula

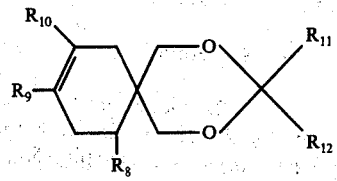

wherein $R_8$, $R_9$ and $R_{10}$ are members selected from the group consisting of hydrogen and methyl, with the proviso that at least one of $R_8$, $R_9$ and $R_{10}$ is methyl, $R_{11}$ is a member selected from the group consisting of hydrogen, alkyl having 1 to 4 carbon atoms, vinyl and 1-propenyl and $R_{12}$ is a member selected from the group consisting of hydrogen and alkyl having 1 to 4 carbon atoms.

These and other objects of the present invention will become more apparent as the description thereof proceeds.

DESCRIPTION OF THE INVENTION

It has been found that 2,4-dioxa-spiro(5,5)undec-8-ens of the following general formula can be used in an advantageous manner as perfumes having a wide variety of fragrances:

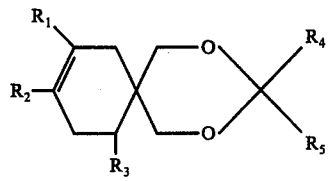

in which $R_1$, $R_2$ and $R_3$ represent hydrogen or a methyl radical, $R_4$ represents hydrogen, an alkyl having 1 to 4 carbon atoms or the radicals $-OCH_3$, $-OC_2H_5$, $-CH=CH_2$ or $-CH=CH-CH_3$, $R_5$ represents hydrogen of an alkyl having 1 to 4 carbon atoms or $R_4$ and $R_5$ together can be closed to form a cycloaliphatic ring system having the ring members $-(CH_2)_n-$ wherein $n$ represents the numbers 4 to 6.

More particularly, the present invention relates to a perfumery composition consisting essentially of from 1 to 50% by weight of a 2,4-dioxa-spiro(5,5)undec-8-en of the formula

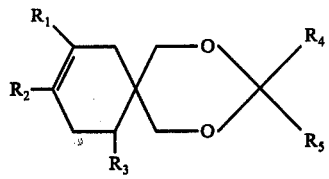

wherein $R_1$, $R_2$ and $R_3$ are members selected from the group consisting of hydrogen and methyl, $R_4$ is a member selected from the group consisting of hydrogen, alkyl having 1 to 4 carbon atoms, methoxy, ethoxy, vinyl and 1-propenyl, $R_5$ is a member selected from the group consisting of hydrogen and alkyl having 1 to 4 carbon atoms, methoxy, ethoxy, vinyl and 1-propenyl, $R_5$ is a member selected from the group consisting of hydrogen and alkyl having 1 to 4 carbon atoms, and $R_4$ and $R_5$ taken together are $-(CH_2)_n-$ where $n$ is an integer from 4 to 6, and the remainder customary constituents of perfumery compositions.

In addition certain of the above 2,4-dioxa-spiro(5,5)undec-8-ens are novel compounds. Particularly these novel compounds are 2,4-dioxa-spiro(5,5)undec-8-ens selected from the group consisting of 3-methyl-2,4-dioxa-spiro(5,5)undec-8-en, 3-ethyl-2,4-dioxa-spiro(5,5)undec-8-en, 3-propyl-2,4-dioxa-spiro(5,5)undec-8-en, 3,3-dimethyl-2,4-dioxa-spiro(5,5)undec-8-en, 3-ethyl-3-methyl-2,4-dioxa-spiro(5,5)undec-8-en, a compound having the formula

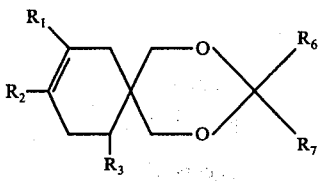

wherein $R_1$, $R_2$ and $R_3$ are members selected from the group consisting of hydrogen and methyl, $R_6$ is a member selected from the group consisting of methoxy and ethoxy, $R_7$ is a member selected from the group consisting of hydrogen and alkyl having 1 to 4 carbon atoms, and $R_6$ and $R_7$ taken together are —$(CH_2)_n$— where $n$ is an integer from 4 to 6, and a compound of the formula

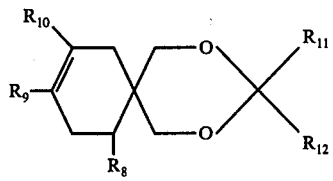

wherein $R_8$, $R_9$ and $R_{10}$ are members selected from the group consisting of hydrogen and methyl, with the proviso that at least one of $R_8$, $R_9$ and $R_{10}$ is methyl, $R_{11}$ is a member selected from the group consisting of hydrogen, alkyl having 1 to 4 carbon atoms, vinyl and 1-propenyl and $R_{12}$ is a member selected from the group consisting of hydrogen and alkyl having 1 to 4 carbon atoms.

The products to be used as perfumes, in accordance with the present invention, are manufactured by known methods. The synthesis, whose principle is known in the literature, is based on the reaction of dienes and α, β-unsaturated aldehydes which cyclize in a Diels-Alder reaction to form tetrahydrobenzaldehydes, as is described by O. Diels and K. Alder in the IIIrd Report on "Synthesen in der hydroaromatischen Reihe" in Liebigs, Ann. Chem.470, pages 62–103 (1929).

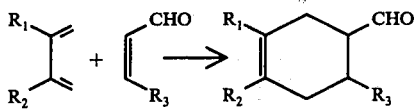

The further reaction of the tetrahydrobenzaldehyde with surplus formaldehyde to form 3-cyclohexene-1,1-dimethanol and its derivatives has already been reported by H. E. French and D. M. Gallagher in J. Amer. Chem. Soc. 64, pages 1497–99 (1942).

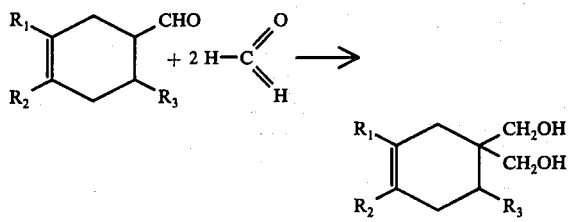

The synthesis of 2,4-dioxa-spiro(5,5)undec-8-ens of the above mentioned general formula from 3-cyclohexene-1,1-dimethanol and its derivatives can be effected by methods known in the literature, such as acid-catalyzed acetalization or ketalization and the azeotropic removal of water of reaction, preferably, however, by re-acetalization or reketalization. Thus, the acetal of 3-cyclohexene-1,1-dimethanol and isobutyraldehyde is mentioned by C. S. Rondestvedt in J. Org. Chem. 26, page 2249 (1961 without further data concerning the possibilities of use and the properties.

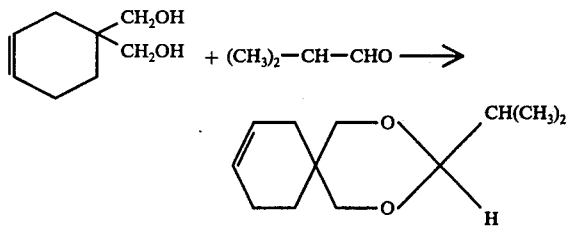

Furthermore, acetals of 3-cyclohexene-1,1-dimethanol with unsaturated aldehydes as intermediate products for the production of high molecular weight epoxidized polyether acetals are, for example, mentioned in German Auslegesschrift (DAS) No. 1,180,530.

A particularly simple variant of the production of the cyclic acetals is described by S. R. Sandler and W. Kawo in Organic Functional Group Preparations, Vol. III, Academic Press 1972, pages 41–42. In accordance with this, the desired spirocyclic acetals and ketals are readily obtained by reacting the diols and aldehydes or ketones with orthoesters in the presence of small quantities of acid.

2,4-dioxa-spiro(5,5)undec-8-ens to be used in accordance with the present invention area, for example, 2,4-dioxa-spiro(5,5)undec-8-en
3-methyl-2,4-dioxa-spiro(5,5)undec-8-en
3-ethyl-2,4-dioxa-spiro(5,5)undec-8-en
3-propyl-2,4-dioxa-spiro(5,5)undec-8-en
3-isopropyl-2,4-dioxa-spiro(5,5)undec-8-en
3-butyl-2,4-dioxa-spiro(5,5)undec-8-en
3,3-dimethyl-2,4-dioxa-spiro(5,5)undec-8-en
3-methyl-3-ethyl-2,4-dioxa-spiro(5,5)undec-8-en
3-vinyl-2,4-dioxa-spiro(5,5)undec-8-en
3-(1-propenyl)-2,4-dioxa-spiro(5,5)undec-8-en
3,3-tetramethylene-2,4-dioxa-spiro(5,5)undec-8-en
8-methyl-2,4-dioxa-spiro(5,5)undec-8-en
9-methyl-2,4-dioxa-spiro(5,5)undec-8-en
11-methyl-2,4-dioxa-spiro(5,5)undec-8-en
3,8-dimethyl-2,4-dioxa-spiro(5,5)undec-8-en
11-methyl-3-isopropyl-2,4-dioxa-spiro(5,5)undec-8-en
3-ethoxy-2,4-dioxa-spiro(5,5)undec-8-en
3-methoxy-2,4-dioxa-spiro(5,5)undec-8-en
3,3-pentamethylene-2,4-dioxa-spiro(5,5)undec-8-en
11-methyl-3-methoxy-2,4-dioxa-spiro(5,5)undec-8-en
3-ethyl-11-methyl-2,4-dioxa-spiro(5,5)undec-8-en
3-isopropyl-11-methyl-2,4-dioxa-spiro(5,5)undec-8-en
3,3,11-trimethyl-2,4-dioxa-spiro(5,5)undec-8-en
3,8and/or 9-dimethyl-2,4-dioxa-spiro(5,5)undec-8-en
3,9-dimethyl-2,4-dioxa-spiro(5,5)undec-8-en
3-ethyl-8 and/or 9-methyl-2,4-dioxa-spiro(5,5)undec-8-en
3-isopropyl-8 and/or 9 methyl-2,4-dioxa-spiro(5,5)undec-8-en
3,3,8 and/or 9-trimethyl-2,4-dioxa-spiro(5,5)undec-8-en
8 and/or 9,11-dimethyl-2,4-dioxa-spiro(5,5)undec-8-en
3,8 and/or 9,11-trimethyl-2,4-dioxa-spiro(5,5)undec-8-en 3-ethyl-8 and/or 9,11-dimethyl-2,4-dioxa-spiro(5,5)undec-8-en
8,9-dimethyl-2,4-dioxa-spiro(5,5)undec-8-en
3,8,9-trimethyl-2,4-dioxa-spiro(5,5)undec-8-en
3-ethyl-8,9-dimethyl-2,4-dioxa-spiro(5,5)undec-8-en
8,9,11-trimethyl-2,4-dioxa-spiro(5,5)undec-8-en
3-ethyl-8,9,11-trimethyl-2,4-dioxa-spiro(5,5)undec-8-en
3-isopropyl-8,9,11-trimethyl-2,4-dioxa-spiro(5,5)undec-8-en
11-methyl-3-methoxy-2,4-dioxa-spiro(5,5-)under-8-en.

Moreover, a large number of the said products constitute new compounds.

The 2,4-dioxa-spiro(5,5)undec-8-ens to be used in accordance with the present invention are valuable perfumes having characteristic fragrances ranging from fruity, herbal, flowery to leather-like. A particular advantage of the compounds is that they are capable of being combined very satisfactorily to form novel fragrances of perfumery compositions in accordance with the present invention.

The 2,4-dioxa-spiro(5,5)undec-8-ens to be used, in accordance with the present invention, as perfumes, can be mixed with other perfumes in a wide range of quantity ratios to form novel perfume compositions. However, in general, the proportion of the 2,4-dioxa-spiro(5,5)undec-8-ens in the perfume compositions will vary from 1 to 50% by weight relative to the total composition. The remainder of the composition is conventional perfume constituents. Such a composition can act directly as a perfume or, alternatively, can be used to perfume cosmetics such as creams, lotions, toilet waters, aerosols, toilet soaps etc. However, as is possible with the 2,4-dioxa-spiro(5,5)undec-8-ens themselves, they can also be used to improve the odor of technical products such as washing and cleaning agents, disinfectants, agents for treating textiles, etc.

The present invention will now be further illustrated by way of the following Examples but without limiting the invention to these Examples.

EXAMPLES

The twenty-eight 2,4-dioxa-spiro(5,5)undec-8-ens specified hereinafter were obtained in accordance with the following general working instructions:

A few granules of p-toluene sulfonic acid were added to the mixture comprising 0.1 mol of 3-cyclohexene-1,1-dimethanol, 0.1 mol of aldehyde, or ketone and 0.1 mol of triethyl orthoformate. The mixture was agitated for several hours at 20° to 40° C. Ethanol and ethyl formate were subsequently distilled off. The residue was dissolved in ether and the solution obtained was washed with aqueous sodium hydroxide solution and water. After separation, the organic phase was dried over sodium sulfate, and the residue after evaporation was distilled in vacuo. The following were obtained in this manner:

EXAMPLE 1

3-methyl-2,4-dioxa-spiro(5,5)undec-8-en

The compound is a colorless oil, boiling point 76° C at 6.0 torr, $n_D^{20} = 1.4777$. The odor is sweet, camphoric, and has a potato and neroli fragrance.

EXAMPLE 2

3-ethyl-2,4-dioxa-spiro(5,5)undec-8-en

The compound is a colorless oil, boiling point 86° C at 6.0 torr, $n_D^{20} = 1.4773$, having a fragrance of roses and catechu.

EXAMPLE 3

3-propyl-2,4-dioxa-spiro(5,5)undec-8-en

The product is a colorless oil, boiling point 86° C at 6.0 torr, $n_D^{20} = 1.4742$, having a fragrance of leather and an anise-like secondary odor.

EXAMPLE 4

3-isopropyl-2,4-dioxa-spiro(5,5)undec-8-en

The compound is a colorless oil, boiling point 81° C at 1.8 torr, $n_D^{20} = 1.4748$, having a spicy herbal odor.

EXAMPLE 5

3,3-dimethyl-2,4-dioxa-spiro(5,5)undec-8-en

The compound is a colorless oil, boiling point 86° C at 7.0 torr, $n_D^{20} = 1.4756$, having a herbal-camphoric fragrance reminiscent of straw.

EXAMPLE 6

3-ethyl-3-methyl-2,4-dioxa-spiro(5,5)undec-8-en

The compound is a colorless oil, boiling point 70° C at 0.9 torr, $n_D^{20} = 1.4780$, and has a characteristic odor which cannot be described.

EXAMPLE 7

3,3-tetramethylene-2,4-dioxa-spiro(5,5)undec-8-en

The compound is a colorless oil, boiling point 104° C at 1.5 torr, $n_D^{20} = 1.5000$, and has a jasmine-like herbal fragrance.

EXAMPLE 8

3-vinyl-2,4-dioxa-spiro(5,5)undec-8-en

The product is a colorless oil, boiling point 245° C at 760 torr, $n_D^{20} = 1.4940$, and has a characteristic odor.

EXAMPLE 9

3,-ethoxy-2,4-dioxa-spiro(5,5)undec-8-en

For the purpose of producing the compound, a small quantity of p-toluene sulfonic acid was added to 14.2 gm (0.1 mol) of 3-cyclohexene-1,1-dimethanol and 14.8 gm (0.1 mol) of triethyl orthoformate and the mixture was agitated for several hours at 40° C. The ethyl alcohol formed was subsequently distilled off and the residue was worked up in the manner already described. A colorless oil was obtained, boiling point 78° C at 0.15 torr, $n_D^{20} = 1.4758$, and had a fruity odor with leather, castoreum and jasmine nuances.

The 2,4-dioxa-spiro(5,5)undec-8-ens given in the following Table were produced in accordance with the general working instructions given at the beginning of the Examples. The products constitute colorless oils, and their physical data and the descriptions of their odors are given in the Table.

TABLE

| Example No. | Chemical Designation | Boiling Point ° C/Torr | $n_D^{20}$ | Description of Odor |
|---|---|---|---|---|
| 10 | 11-methyl-2,4-dioxa-spiro(5,5) | 67/1.0 | 1.4881 | Herbal, woody very natural |

TABLE-continued

| Example No. | Chemical Designation | Boiling Point °C/Torr | $n_D^{20}$ | Description of Odor |
|---|---|---|---|---|
| 11 | undec-8-en 3,11-dimethyl-2,4-dioxa-spiro(5.5)undec-8-en | 60/0.2 | 1.4804 | Green, thujon fragrance, for rosemary-lavanduline compositions |
| 12 | 3-ethyl-11-methyl-2,4-dioxa-spiro(5,5)undec-8-en | 61/0.1 | 1.4788 | Green, fragrance of buds |
| 13 | 3-isopropyl-11-methyl-2,4-dioxa-spiro(5,5)undec-8-en | 66/0.08 | 1.4768 | Rose oxide, geranium fragrance |
| 14 | 3,3,11-trimethyl-2,4-dioxa-spiro(5,5)undec-8-en | 64/0.1 | 1.4778 | Camphoric, woody, fruity, vevdox-fragrance |
| 15 | 3,8/9-dimethyl-2,4-dioxa-spiro(5,5)undec-8-en | 75/1.5 | 1.4773 | Fruity, green, herbal, anise fragrance |
| 16 | 3,9-dimethyl-2,4-dioxa-spiro(5,5)undec-8-en | 85/5.0 | 1.4772 | Gardenia, petitgrain fragrance, green |
| 17 | 3-ethyl-8/9-methyl-2,4-dioxa-spiro(5,5)undec-8-en | 74/0.05 | 1.4769 | Rose fragrance |
| 18 | 3-isopropyl-8/9-methyl-2,4-dioxa-spiro(5,5)undec-8-en | 74/0.4 | 1.4740 | Rose fragrance, very natural |
| 19 | 3,3,8/9-trimethyl-2,4-dioxa-spiro(5,5)undec-8-en | 81/1.5 | 1.4759 | Woody, pine fragrance, fresh, sawdust |
| 20 | 8/9,11-dimethyl-2,4-dioxa-spiro(5,5)undec-8-en | 88/2.4 | 1.4875 | Herbal, woody, rosemary fragrance |
| 21 | 3,8/9,11-trimethyl-2,4-dioxa-spiro(5,5)undec-8-en | 70/0.6 | 1.4790 | Sweaty, borneol-like camphoric, onion-like |
| 22 | 3-ethyl-8/9,11-dimethyl-2,4-dioxa-spiro(5,5)undec-8- | 68/0.05 | 1.4788 | Natural forest soil, odor, rose fragrance |
| 23 | 8,9-dimethyl-2,4-dioxa-spiro(5,5)undec-8-en | 70/0.1 | 1.4908 | Salicylate, quinoline, neroli fragrance |
| 24 | 3,8,9-trimethyl-2,4-dioxa-spiro(5.5)undec-8-en | 58/0.05 | 1.4822 | Herbal, petit-grain fragrance |
| 25 | 3-ethyl-8,9-dimethyl-2,4-dioxa-spiro(5,5)undec-8-en | 73/0.05 | 1.4816 | Earthy, petit-grain fragrance |
| 26 | 8,9,11-trimethyl-2,4-dioxa-spiro(5,5)undec-8-en | 62/0.05 | 1.4910 | Spicey, thyme fragrance |
| 27 | 3-ethyl-8,9,11-trimethyl-2,4-dioxa-spiro(5,5)undec-8-en | 75/0.1 | 1.4826 | Woody, green |
| 28 | 3-isopropyl-8,9 11-trimethyl-2,4-dioxa-spiro(5,5)undec-8-en | 88/0.1 | 1.4804 | Flowery |

8/9 designates one substituent in the 8 or 9 position or on a mixture of 8 and 9 positions All the compounds given in the above Examples have the described fragrances with excellent clinging properties or persistency which render them suitable for producing a wide variety of perfume compositions. Such compositions can be used to perfume a wide variety of products such as cosmetics, washing agents, soaps as well as technical products in concentrations of approximately 0.05 to 2% by weight. Examples of perfumery compositions having a content of the 2,4-dioxa-spiro(5,-5)undec-ens in accordance with the invention are given hereinafter.

EXAMPLE 29

| Herb Complex | Parts by Weight |
|---|---|
| 2-isopropyl-2,4-dioxa-spiro(5,5)undec-8-en | 100 |
| Cedar wood oil | 200 |
| Lavandine oil | 100 |
| Geranium oil, artificial | 100 |
| Rosemary oil, spanish | 50 |
| Linalool, synthetic | 50 |
| Terpinyl acetate | 50 |
| Patchouli oil | 50 |
| Cumarin | 40 |
| Herbal perfume 63 180 (H&R) | 80 |
| Thyme oil, white | 20 |
| Cassia oil, chinese | 20 |
| Sandal (H&R) | 20 |
| Moss base AB 311 (PPL) | 30 |
| Carnation leaf oil | 20 |
| Hay oil | 20 |
| Musk ambrette | 20 |
| Mugwort oil | 20 |
| Salicylaldehyde, 10% | 10 |
| | 1000 |

EXAMPLE 30

| Jasmine Complex | Parts by Weight |
|---|---|
| 3-ethoxy-2,4-dioxa-spiro(5,5)undec-8-en | 200 |
| Hydroxycitronellal | 200 |
| Benzyl acetate | 100 |
| Linalool | 100 |
| Benzyl alcohol | 60 |
| Lyral | 50 |
| α-amylcinnamaldehyde | 50 |
| Ylang-ylang oil | 60 |
| Phenylethyl isobutyrate | 25 |
| Geranyl acetate | 20 |
| Phenylethyl alcohol | 20 |
| Dimethylbenzylcarbinyl acetate | 20 |
| Phytol | 20 |
| Benzylphenyl acetate | 20 |
| Benzyl butyrate | 10 |
| Terpineol | 10 |
| Geraniol | 10 |
| Nerolidol | 10 |
| Eugenol | 5 |
| Methyl anthranilate | 5 |
| Decalactone | 2 |
| Indole | 2 |
| Decanal, 10% | 1 |
| | 1000 |

EXAMPLE 31

| Rose-geranium Complex | Parts by Weight |
|---|---|
| 3-ethyl-2,4-dioxa-spiro(5,5)undec-8-en | 300 |
| Phenylethyl alcohol | 200 |
| Geranium oil Bourbon | 200 |
| Geraniol ex palmarosa oil | 100 |
| Patchouli oil | 50 |
| Civet extract, 10% | 50 |
| Styrax honduras | 40 |
| Musk zylene | 60 |
| | 1000 |

The preceding specific embodiments are illustrative of the practice of the invention. It is to be understood however, that other expedients known to those skilled in the art of disclosed herein, may be employed without departing from the spirit of the invention or the scope of the appended claims.

We claim:

1. A perfumery composition consisting essentially of from 1 to 50% by weight of a 2,4-dioxa-spiro(5,5)undec-8-en of the formula

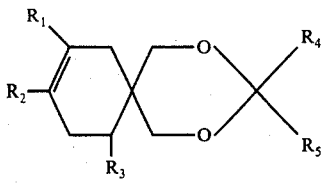

wherein $R_1$, $R_2$ and $R_3$ are members selected from the group consisting of hydrogen and methyl, $R_4$ is a member selected from the group consisting of hydrogen, alkyl having 1 to 4 carbon atoms, methoxy, ethoxy, vinyl and 1-propenyl, $R_5$ is a member selected from the group consisting of hydrogen and alkyl having 1 to 4 carbon atoms, methoxy, ethoxy, vinyl and 1-propenyl, $R_5$ is a member selected from the group consisting of hydrogen and alkyl having 1 to 4 carbon atoms, and $R_4$ and $R_5$ taken together are —$(CH_2)_n$— where $n$ is an integer from 4 to 6, and the remainder customary constituents of perfumery compositions.

2. A perfumery composition as claimed in claim 1, which comprises at least one perfume other than said 2,4-dioxa-spiro(5,5)undec-8-en.

3. The perfume composition of claim 1 wherein the 2,4-dioxa-spiro(5,5)undec-8-en which is 3-methyl-2,4-dioxa-spiro(5,5)undec-8-en.

4. The perfume composition of claim 1 wherein the 2,4-dioxa-spiro(5,5)undec-8-en which is 3-ethyl-2,4-dioxa-spiro(5,5)undec-8-en.

5. The perfume composition of claim 1 wherein the 2,4-dioxa-spiro(5,5)undec-8-en which is 3-propyl, 2,4-dioxa-spiro(5,5)undec-8-en.

6. The perfume composition of claim 1 wherein the 2,4-dioxa-spiro(5,5)undec-8-en which is 3,3-dimethyl-2,4-dioxa-spiro(5,5)undec-8-en.

7. The perfume composition of claim 1 wherein the 2,4-dioxa-spiro(5,5)undec-8-en which is 3-ethyl-3-methyl-2,4-dioxa-spiro(5,5)undec-8-en.

8. The perfume composition of claim 1 wherein the 2,4-dioxa-spiro(5,5)undec-8-en which is 3,3-tetramethylene-2,4-dioxa-spiro(5,5)undec-8-en.

9. The perfume composition of claim 1 wherein the 2,4-dioxa-spiro(5,5)undec-8-en which is 3-ethoxy-2,4-dioxa-spiro(5,5)undec-8-en.

10. The perfume composition of claim 1 wherein the 2,4-dioxa-spiro(5,5)undec-8-en which is 11-methyl-2,4-dioxa-spiro(5,5)undec-8-en.

11. The perfume composition of claim 1 wherein the 2,4-dioxa-spiro(5,5)undec-8-en which is 3,11-dimethyl-2,4-dioxa-spiro(5,5)undec-8-en.

12. The perfume composition of claim 1 wherein the 2,4-dioxa-spiro(5,5)undec-8-en which is 3-ethyl-11-methyl-2,4-dioxa-spiro(5,5)undec-8-en.

13. The perfume composition of claim 1 wherein the 2,4-dioxa-spiro(5,5)undec-8-en which is 3-isopropyl-11-methyl-2,4-dioxa-spiro(5,5)undec-8-en.

14. The perfume composition of claim 1 wherein the 2,4-dioxa-spiro(5,5)undec-8-en which is 3,3,11-trimethyl-2,4-dioxa-spiro(5,5)undec-8-en.

15. The perfume compositin of claim 1 wherein the 2,4-dioxa-spiro(5,5)undec-8-en which is 3,8/9-dimethyl-2,4-dioxa-spiro(5,5)undec-8-en.

16. The perfume composition of claim 1 wherein the 2,4-dioxa-spiro(5,5)undec-8-en which is 3,9-dimethyl-2,4-dioxa-spiro(5,5)undec-8-en.

17. The perfume composition of claim 1 wherein the 2,4-dioxa-spiro(5,5)undec-8-en which is 3-ethyl-8/9-methyl-2,4-dioxa-spiro(5,5)undec-8-en.

18. The perfume composition of claim 1 wherein the 2,4-dioxa-spiro(5,5)undec-8-en which is 3-isopropyl-8/9-methyl-2,4-dioxa-spiro(5,5)undec-8-en.

19. The perfume composition of claim 1 wherein the 2,4-dioxa-spiro(5,5)undec-8-en which is 3,3,8/9-trimethyl-2,4-dioxa-spiro(5,5)undec-8-en.

20. The perfume composition of claim 1 wherein the 2,4-dioxa-spiro(5,5)undec-8-en which is 8/9,11-dimethyl-2,4-dioxa-spiro(5,5)undec-8-en.

21. The perfume composition of claim 1 wherein the 2,4-dioxa-spiro(5,5)undec-8-en which is 3,8/9,11-trimethyl-2,4-dioxa-spiro(5,5)undec-8-en.

22. The perfume composition of claim 1 wherein the 2,4-dioxa-spiro(5,5)undec-8-en which is 3-ethyl-8/9,11-dimethyl-2,4-dioxa-spiro(5,5)undec-8-en.

23. The perfume composition of claim 1 wherein the 2,4-dioxa-spiro(5,5)undec-8-en which is 8,9-dimethyl-2,4-dioxa-spiro(5,5)undec-8-en.

24. The perfume composition of claim 1 wherein the 2,4-dioxa-spiro(5,5)undec-8-en which is 3,8,9-trimethyl-2,4-dioxa-spiro(5,5)undec-8-en.

25. The perfume composition of claim 1 wherein the 2,4-dioxa-spiro(5,5)undec-8-en which is 3-ethyl-8,9-dimethyl-2,4-dioxa-spiro(5,5)undec-8-en.

26. The perfume composition of claim 1 wherein the 2,4-dioxa-spiro(5,5)undec-8-en which is 8,9,11-trimethyl-2,4-dioxa-spiro(5,5)undec-8-en.

27. The perfume composition of claim 1 wherein the 2,4-dioxa-spiro(5,5)undec-8-en which is 3-ethyl-8,9,11-trimethyl-2,4-dioxa-spiro(5,5)undec-8-en.

28. The perfume composition of claim 1 wherein the 2,4-dioxa-spiro(5,5)undec-8-en which is 3-isopropyl-8,9,11-trimethyl-2,4-dioxa-spiro(5,5)undec-8-en.

* * * * *

UNITED STATES PATENT OFFICE
CERTIFICATE OF CORRECTION

Patent No. 4,113,664          Dated   Sept. 12, 1978

Inventor(s) JENS CONRAD and KLAUS BRUNS

It is certified that error appears in the above-identified patent and that said Letters Patent are hereby corrected as shown below:

| Col. | Line | |
|---|---|---|
| 1 | 27-29 | "$R_5$ is a member selected from the group consisting of hydrogen and alkyl having 1 to 4 carbon atoms, methoxy, ethoxy, vinyl and 1-propenyl", should be cancelled |
| 2 | 29 | "of" should be —or— |
| 2 | 51-53 | Same as Col. 1 |
| 4 | 6 | "(1961" should be —(1961)— |
| 4 | 33 | "area" should be —are— |
| 7 | 38 | "undec-8-" should be —undec-8-en— |
| Claim 1 | | |
| 9 | 15-17 | Same as Col. 1 |

Signed and Sealed this

Twenty-sixth Day of February 1980

[SEAL]

Attest:

SIDNEY A. DIAMOND

Attesting Officer          Commissioner of Patents and Trademarks